United States Patent
Sener et al.

(10) Patent No.: US 11,850,313 B2
(45) Date of Patent: Dec. 26, 2023

(54) METHOD AND COMPOSITIONS FOR PROTECTING TISSUE

(71) Applicant: The London Health Sciences Centre Research Inc., London (CA)

(72) Inventors: Alp Sener, London (CA); Smriti Juriasingani, Mississauga (CA)

(73) Assignee: The London Health Sciences Centre Research Inc., London (CA)

( * ) Notice: Subject to any disclaimer, the term of this patent is extended or adjusted under 35 U.S.C. 154(b) by 483 days.

(21) Appl. No.: 17/127,965

(22) Filed: Dec. 18, 2020

(65) Prior Publication Data
US 2021/0260226 A1 Aug. 26, 2021

Related U.S. Application Data

(60) Provisional application No. 62/951,578, filed on Dec. 20, 2019.

(51) Int. Cl.
| | |
|---|---|
| *A01N 1/02* | (2006.01) |
| *A61K 31/67* | (2006.01) |
| *A61K 33/04* | (2006.01) |
| *A61K 35/14* | (2015.01) |
| *A61K 38/42* | (2006.01) |
| *A61L 2/00* | (2006.01) |

(52) U.S. Cl.
CPC .......... *A61L 2/0088* (2013.01); *A01N 1/0226* (2013.01); *A61K 31/67* (2013.01); *A61K 33/04* (2013.01); *A61K 35/14* (2013.01); *A61K 38/42* (2013.01)

(58) Field of Classification Search
CPC ...... A61K 31/385; A61K 31/67; A61K 33/04; A61K 35/14; A61K 38/42; A01N 1/0205; A01N 1/021
See application file for complete search history.

(56) References Cited

U.S. PATENT DOCUMENTS

| | | | |
|---|---|---|---|
| 2015/0196034 A1* | 7/2015 | Wood | A61P 3/06 549/7 |
| 2018/0256639 A1* | 9/2018 | Sherman | A61P 9/10 |
| 2021/0195887 A1* | 7/2021 | Hatayama | A01N 1/0247 |

OTHER PUBLICATIONS

Szczesny B, et al., AP39, a novel mitochondria-targeted hydrogen sulfide donor, stimulates cellular bioenergetics, exerts cytoprotective effects and protects against the loss of mitochondrial DNA integrity in oxidatively stressed endothelial cells in vitro. Nitric Oxide. Sep. 15, 2014;41: 120-30.

Juriasingani S, et al., H2S supplementation: A novel method for successful organ preservation at subnormothermic temperatures. Nitric Oxide [Internet]. Dec. 1, 2018 [cited Feb. 10, 2019];81:57-66.

Juriasingani S, Akbari M, Luke P, Sener A. Novel therapeutic strategies for renal graft preservation and their potential Impact on the future of clinical transplantation [Internet]. vol. 24, Current Opinion in Organ Transplantation. Lippincott Williams and Wilkins; 2019 [cited Apr. 7, 2020]. p. 385-90.

Bhattacharjee RN, Ruthirakanthan A, Sun Q, Richard-Mohamed M, Luke S, Jiang L, Aquil S, Sharma H, Tun-Abraham ME, Alharbi B, Haig A, Sener A, Luke PPW. Subnormothermic Oxygenated Perfusion Optimally Preserves Donor Kidneys Ex Vivo. Kidney Int Reports. Sep. 1, 2019;4(9):1323-33.

Bhattacharjee RN, et al., Renal Protection Against Ischemia Reperfusion Injury: Hemoglobin-based Oxygen Carrier-201 Versus Blood as an Oxygen Carrier in Ex Vivo Subnormothermic Machine Perfusion. Transplantation. Mar. 2020, 104(3): 482-489.

Hoyer DP, Gallinat A, Swoboda S, Wohlschläger J, Rauen U, Paul A, Minor T. Subnormothermic machine perfusion for preservation of porcine kidneys in a donation after circulatory death model. Transpl Int [Internet]. Oct. 2014 [cited Apr. 12, 2018];27(10):1097-106.

* cited by examiner

*Primary Examiner* — Jeffrey E. Russel
(74) *Attorney, Agent, or Firm* — Eduardo Krupnik (57) ABSTRACT

A tissue oxygenation composition comprising (a) an oxygenated solution or a solution containing an oxygen carrier and (b) hydrogen sulfide ($H_2S$). The disclosure also relates to methods of preserving, reperfusing and/or transfusing tissue with a tissue oxygenation composition according to the present disclosure.

20 Claims, 8 Drawing Sheets

Hemopure-21°C
Fig. 6A

Hemopure + 200nM AP39-21°C
Fig. 6B

SCS-4°C
Fig. 6C

Hemopure + 1uM AP39-21°C
Fig. 6D

Hemopure + 150uM STS-21°C
Fig. 6E

Fig. 6F

Hemopure-21°C

Fig. 7A

Hemopure + 200nM AP39-21°C

Fig. 7B

SCS-4°C

Fig. 7C

Hemopure + 1uM AP39-21°C

Fig. 7D

Hemopure + 150uM STS-21°C

METHOD AND COMPOSITIONS FOR PROTECTING TISSUE

FIELD OF THE INVENTION

This disclosure generally relates to methods and compositions for tissue and/or organ preservation. In certain embodiments, there are methods and compositions for preserving tissue and/or organs at subnormothermic or normothermic temperatures.

BACKGROUND

The global incidence of end stage renal disease is on the rise and kidney transplantation is the treatment of choice. Due to the high demand for donor kidneys, there is an increasing need for strategies that improve transplant outcomes and expand the pool of acceptable donor organs. Living donors are preferred for optimal organ transplant outcomes. To bridge the gap between organ supply and demand, donation after cardiac death (DCD) donors and other extended criteria donors (ECD) are being used more frequently. However, grafts from such donors often display worse outcomes post-transplantation. One of the factors that influences transplant outcomes and contributes to the preference for living organ donors is ischemia-reperfusion injury (IRI). IRI is an inevitable consequence of the loss and subsequent gain of blood flow during transplantation. It is important to consider IRI and its effects because it has been associated with delayed graft function (DGF), acute kidney injury, acute graft rejection and early graft loss. IRI is an especially important factor to consider with DCD kidneys because they experience prolonged warm ischemia during cardiac arrest while the organ is in the donor and they have an increased incidence of DGF. Optimal preservation of the donor organ prior to transplantation is essential for mitigating the effects of IRI. Current organ perseveration methods typically involve hypothermic conditions that lower the metabolic activity of the donor organ. This allows for better survival in hypoxic conditions. The most common organ preservation method is static cold storage where an organ is placed in a preservation solution and then stored on ice. Currently, University of Wisconsin (UW) solution is the gold standard for preservation solutions. However, hypothermic preservation causes cold IRI, which has been linked to DGF, increased acute tubular necrosis (ATN) and decreased graft survival.

Small, endogenously produced molecules known as gasotransmitters have recently been identified as a potential therapeutic agent to mitigate renal IRI. This class of molecules includes carbon monoxide (CO), nitric oxide (NO) and most recently, hydrogen sulfide ($H_2S$). $H_2S$ has been shown to have a variety of cytoprotective effects. In terms of mitigating the effects of renal IRI, AP39 shows greater potential because it is targeted to the mitochondria, which are key players in IRI, via its triphenylphosphonium motif. Using various models, our group has shown that adding mitochondria-targeted $H_2S$ donor AP39 to University of Wisconsin (UW) solution during static cold storage (4° C.) of donor kidneys improves graft outcomes. However, despite being the clinical standard of care, cold storage in UW solution leads to poor graft outcomes, particularly for sub-optimal organs obtained from donation after cardiac death (DCD) donors. As a result, there is a growing interest in normothermic (37° C.) and subnormothermic preservation (18-35° C.), but existing techniques are complicated and expensive.

Whiteman and Szabo (Nitric Oxide 2014) indicated that AP39 provides a cryoprotective effect under oxidative stress conditions including a protection against oxidative mitochondrial DNA damage. A follow-up publication by Juriasingani, Whiteman and Sener (Nitric Oxide 2018) showed that AP39 supplementation improves kidney preservation in UW solution for subnormothermic temperatures (21° C.). However, neither UW nor AP39 is known to oxygenate tissue.

The use of $H_2S$ in a solution to oxygenate tissue and improve tissue metabolism is counterintuitive. U.S. Pat. No. 7,993,681 (U.S. '681) describes the use of $H_2S$ with UW as a preservation agent for inducing stasis in tissues and organs. U.S. '681 uses $H_2S$ as an oxygen antagonist to induce stasis. According to U.S. '681 stasis is at least a two-fold reduction in the rate or amount of oxygen consumption. U.S. '681 lists $H_2S$ as an oxygen antagonist. That is, $H_2S$ is used to reduce tissue oxygenation, and it would be counter intuitive to use $H_2S$ in a solution to oxygenate tissue.

Thus, a need exists to preserve tissues in oxygenated conditions using blood or blood substitutes at subnormothermic and normothermic temperatures. This disclosure satisfies this need and provides related advantages as well.

SUMMARY

In one embodiment, the present disclosure provides for a tissue oxygenation composition comprising (a) an oxygenated solution or a solution containing an oxygen carrier and (b) hydrogen sulfide ($H_2S$).

In one embodiment of the tissue oxygenation composition of the present disclosure, the composition comprises the solution containing the oxygen carrier, and wherein the oxygen carrier is a natural or synthetic molecule that can effectively transport and deliver oxygen to tissues and deliver oxygen to tissues.

In another embodiment of the tissue oxygenation composition of the present disclosure, the composition comprises the solution containing the oxygen carrier, and wherein the oxygen carrier is a solution containing red blood cells or hemoglobin.

In another embodiment of the tissue oxygenation composition of the present disclosure, the composition comprises the solution containing the oxygen carrier, and wherein the oxygen carrier is an artificial oxygen carrier.

In another embodiment of the tissue oxygenation composition of the present disclosure, the artificial oxygen carrier is a hemoglobin-based oxygen carrier (HBOC), perfluorocarbon-based oxygen carrier (PFOC) or an artificial oxygen carrier derived from stem cells (SCs).

In another embodiment of the tissue oxygenation composition of the present disclosure, the $H_2S$ is provided as a $H_2S$ donor.

In another embodiment of the tissue oxygenation composition of the present disclosure, the $H_2S$ donor is AP39 or STS.

In another embodiment of the tissue oxygenation composition of the present disclosure, the composition comprises the solution containing the oxygen carrier, the oxygen carrier is a hemoglobin-based oxygen carrier or blood, and wherein the $H_2S$ is provided as a $H_2S$ donor.

In another embodiment, the present disclosure provides for a method of preserving or reperfusing tissue, the method comprising storing or reperfusing the tissue with the tissue oxygenation composition according to any embodiment of the present disclosure.

In one embodiment of the method of preserving or reperfusing tissue, the tissue oxygenation composition comprises the solution containing the oxygen carrier, the oxygen carrier is a hemoglobin-based oxygen carrier or blood, and wherein the $H_2S$ is provided as a $H_2S$ donor.

In another embodiment of the method of preserving or reperfusing tissue, the storing or reperfusing is carried out at subnormothermic temperatures or normothermic temperatures.

In another embodiment, the present disclosure relates to a method of maintaining tissue oxygenation during tissue preservation or reperfusion, the method comprising storing or reperfusing the tissue with a tissue oxygenation composition according to any of the embodiments of the present disclosure.

In one embodiment of the method of maintaining tissue oxygenation during tissue preservation or reperfusion, the composition comprises the solution containing the oxygen carrier, the oxygen carrier is a hemoglobin-based oxygen carrier or blood, and wherein the $H_2S$ is provided as a $H_2S$ donor.

In another embodiment of the method of maintaining tissue oxygenation during tissue preservation or reperfusion, the storing or reperfusing is carried out at subnormothermic temperatures or normothermic temperatures.

In another embodiment, the present disclosure relates to a method of decreasing the incidence and duration of delayed graft function during organ transplantation, the method comprising contacting the organ to be transplanted to a tissue oxygenation composition according to any of the embodiments of this disclosure.

In one embodiment of the method of decreasing the incidence and duration of delayed graft function during organ transplantation of the present disclosure, the tissue oxygenation composition comprises the solution containing the oxygen carrier, the oxygen carrier is a hemoglobin-based oxygen carrier or blood, and wherein the $H_2S$ is provided as a $H_2S$ donor.

In another embodiment of the method of decreasing the incidence and duration of delayed graft function during organ transplantation of the present disclosure, the contacting is carried out at subnormothermic temperatures or normothermic temperatures.

In another embodiment, the present disclosure relates to a method of treating an ischemic event in a subject, the method comprising administering to the subject or contacting a tissue of the subject with a tissue oxygenation composition according to any of the embodiments of this disclosure.

In one embodiment of the method of treating an ischemic event in a subject, the ischemic event is an ischemic injury.

In another embodiment of the method of treating an ischemic event in a subject, the ischemic event includes myocardial infarction, trauma, hypovolemic shock, compartment syndrome, stroke, or sepsis.

DETAILED DESCRIPTION

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices and materials are now described. All technical and patent publications cited herein are incorporated herein by reference in their entirety. Nothing herein is to be construed as an admission that the disclosure is not entitled to antedate such disclosure by virtue of prior disclosure.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure. Embodiments defined by each of these transition terms are within the scope of this disclosure.

Tissues or Biological material contemplated for use with the present disclosure include tissues derived from invertebrates and vertebrates, including mammals; biological materials includes full organisms. In addition to humans, the disclosure can be employed with respect to tissues or biological materials of mammals of veterinary or agricultural importance including those from the following classes: canine, feline, equine, bovine, ovine, murine, porcine, caprine, rodent, lagomorph, lupine, and ursine. The disclosure also extends to fish and birds. Tissues include whole or part of organs. Tissues or biological materials may also be used to refer to a body part in need of the compositions and methods of the present disclosure.

"Subnormothermic temperatures" means temperatures ranging from about 18 to about 35° C. "Normothermic temperatures" means normal body temperature.

A "subject" is a cell or an animal such as a mammal or a human.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder.

To "prevent" intends to prevent a disorder or effect in vitro or in vivo in a system or subject that is predisposed to the disorder or effect. An example of such is preventing the formation of a biofilm in a system that is infected with a microorganism known to produce one.

"Pharmaceutically acceptable carriers" refers to any diluents, excipients or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

"Administration" can be carried out in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

Tissue Preservation, Reperfusion and Transfusion

In one embodiment, the present disclosure provides compositions for tissue preservation, reperfusion and transfusion. The preservation/reperfusion/transfusion compositions of the present disclosure include, in one embodiment, (a) an oxygenated solution or a solution containing an oxygen carrier and (b) hydrogen sulfide ($H_2S$).

In aspects of the disclosure the oxygen carrier is a hemoglobin-based oxygen carrier. In other aspects of the disclosure, the $H_2S$ is provided as a $H_2S$ donor. Non-limiting examples of $H_2S$ donors include AP39 and sodium thiosulfate.

The compositions of the present disclosure have been shown to improve tissue metabolic outcome as compared to current clinical standard of care for organ preservation, reperfusion and transfusion (See FIGS. 2, 3 and 5), while preventing tissue injury. It is well known that one of the most important parameters that reflect proper organ perfusion is the hourly urine output. The Applicants have shown that tissues treated with the compositions of the present disclosure significantly increased urine output relative to the current clinical standard of care (see FIGS. 2 and 5). In addition, tissues treated with the compositions of the present disclosure showed similar or even improved oxygenation and reduced apoptosis injury and necrosis than the current clinical standard of care.

As such, in embodiments, the present disclosure provides for methods of preserving, perfusing, reperfusing and tansfusing tissues (including tissue grafts, part of an organ or whole organs, part of body parts or whole body parts) using the compositions of the present disclosure.

$H_2S$

Hydrogen sulfide ($H_2S$) is a potentially toxic gas that is often associated with petrochemical and natural gas, sewage, paper pulp, leather tanning, and food processing. The primary effect, at the cellular level, appears to be inhibition of cytochrome oxidase and other oxidative enzymes, resulting in cellular hypoxia. Exposure to extreme levels (500 ppm) results in sudden collapse and unconsciousness, a so-called "knockdown" effect, followed by recovery. Post-exposure effects may persist for years, and include loss of coordination, memory loss, motor dysfunction, personality changes, hallucination and insomia. $H_2S$ can be provided as $H_2S$ or as a $H_2S$ donor. Non-limiting examples of $H_2S$ donors include AP39 and sodium thiosulfate.

Typical levels of hydrogen sulfide contemplated for use in accordance with present disclosure include about nM-uM concentrations of slow-releasing $H_2S$ donors. For mitochondria-targeted donors, such as AP39, an effective range of 100-300 nM. For other $H_2S$ donors, concentrations in nM-uM ranges have been reported to be effective. In all cases, the safety and effective dose of the donor molecules has been established in high mammals or in the context of other human pathologies.

Oxygenated Solution and Oxygen Carrier

In this document, an Oxygen Carrier is defined as a natural or synthetic molecule that can effectively transport and deliver oxygen to tissues. Examples of natural molecules that can effectively transport and deliver oxygen to tissues include hemoglobin in red blood cells. Examples of synthetic/artificial molecules that can effectively transport and deliver oxygen to tissues include hemoglobin-based oxygen carriers (HBOCs), perfluorocarbon-based oxygen carriers (PFOCs) and artificial oxygen carriers (AOCs) derived from stem cells (SCs). Examples of Hemoglobin Based Oxygen Carrier, (HBOC) include Hemopure® (HBO2 Therapeutics LLC). HBOC-201 is a polymerized bovine-hemoglobin-based oxygen carrier that has been successfully used in liver and kidney subnormothermic machine perfusion (SMP) and NMP protocols. Further examples of AOCs are found in Ferenz, K. B., et al., J Pharmacol Exp Ther 369:300-310, May 2019, the contents of which are incorporated herein by reference.

The term "oxygenated solution" means a solution into which oxygen has been artificially added.

Advantages

Conventionally, normothermic and subnormothermic kidney perfusion are done with blood. Considering the ever-increasing shortage of blood, however, in embodiments, the compositions of the present disclosure allow to circumvent the use of blood in organ preservation. Additionally, there is a shortage of clinically approved $H_2S$ therapeutics. Many research groups have shown the diverse protective effects of AP39 in various contexts, including renal ischemia reperfusion injury and renal graft preservation. In embodiments, the compositions of the present disclosure facilitate the delivery of $H_2S$ during blood-free perfusion, which will maximize renal graft viability and limit the use of blood for tissue preservation, including renal graft preservation.

In addition to organ preservation, the compositions of the present disclosure lend themselves to other clinical uses such as transfusion of oxygen carrier whole blood substitutes, acute limb ischemia, acute myocardial infarction, acute ischemic stroke, by example; thus potentially adding to the very limited therapeutic armamentarium physicians have in these life threatening scenarios. As such, in embodiments, the compositions of the present disclosure are used in methods to treat an ischemic event, including hypoxic/injury states, such as myocardial infarction, trauma, hypovolemic shock, compartment syndrome and so forth. The method, in embodiments, comprises administering to a subject in need or contacting a tissue of the subject with an effective amount of any of the compositions of the present disclosure.

The following example is intended to illustrate, but not limit the disclosure.

Example 1

Materials and Methods

Animal Description and Care

Pigs weighing 55-65 kg were used for this study. The animals were maintained in accordance with the Committee on the Care and Use of Laboratory Animals appointed by the National Research Council. The animals were housed at the animal facility in the West Valley Building, which is managed by the Animal Care and Veterinary Services Department at The University of Western Ontario. The experimental protocol and housing conditions followed the guidelines of the university's Animal Care Committee and the Canadian Council on Animal Care.

Surgery & Induction of Warm Ischemia to Mimic Donation after Cardiac Death

Pigs were tranquilized prior to transport to the Canadian Surgical Technologies & Advanced Robotics facility (CSTAR, University Hospital, London, Canada). Upon arrival at CSTAR, the animals were prepared for surgery as per SOP. A midline incision was used to expose the kidneys. The right and left kidneys with their ureters were dissected free from the retro peritoneum while leaving the blood supply to the ureter intact and then the ureter was divided. The renal vascular pedicles were left as long as possible by freeing the renal artery and vein up to the aorta and vena cava. The pedicles were clamped for 30 minutes to induce warm ischemia in the donor organs following intravenous infusion of 10000 units of heparin. The injury inflicted is likely greater than that of conventional DCD kidneys after withdrawal of life support as the blood supply is cutoff completely by clamping, which is more harmful than the gradual ischemic injury that occurs during cardiac death. Subsequently, nephrectomies of the left and right kidney were performed and the donor animal was euthanized. All the surgeries were performed by transplant fellows at University Hospital, London, Ontario, Canada.

Ex Vivo Organ Preservation Treatments & Reperfusion to Mimic Transplantation

Figure 4A:
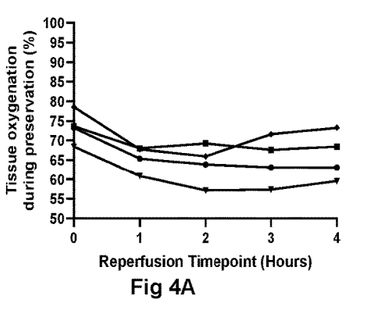
FIGS. 4A-4B. Mean tissue oxygenation during preservation and reperfusion. (A) Tissue oxygenation (%) during 4 h of preservation perfusion with Hemopure®, Hemopure®+200 nM AP39, Hemopure®+1 µM AP39 or Hemopure®+150 µM STS at 21° C. (B) Tissue oxygenation (%) during 4 h of reperfusion with Hemopure® and nutrients at 37° C. after 4 h of preservation via SCS on ice at 4° C. or perfusion with Hemopure®, Hemopure®+200 nM AP39, Hemopure®+1 µM AP39 or Hemopure®+150 µM STS at 21° C. Points in (A) and (B) reflect mean tissue oxygenation values for each group at a specific timepoint. Values were compared using one-way ANOVA. *, $p<0.05$. **, $p<0.01$.

The kidneys were randomly assigned to one of five preservation treatments. The first group of kidneys were flushed with and stored in HTK solution on ice for 4 h (SCS), which reflects the current clinical standard of care for organ preservation. The second group of kidneys were flushed with HTK solution and treated to 4 h of subnormothermic perfusion at 21° C. with Hemopure®. The third group of kidneys were flushed with HTK solution supplemented with 200 nM AP39 and treated to 4 h of subnormothermic perfusion at 21° C. with Hemopure® supplemented with 200 nM AP39. The fourth group of kidneys were flushed with HTK solution supplemented with 1 µM AP39 and treated to 4 h of subnormothermic perfusion at 21° C. with Hemopure® supplemented with 1 µM AP39. The fifth group of kidneys were flushed with HTK solution supplemented with 150 µM STS and treated to 4 h of subnormothermic perfusion at 21° C. with Hemopure® supplemented with 150 µM STS. After the 4 h preservation period, all kidneys were perfused with Hemopure® for 4 h at 37° C. with nutrients to simulate reperfusion after renal transplantation. The kidneys were perfused using an ex vivo perfusion apparatus (FIG. 4). The perfusion pressure was maintained at 50 mmHg. Hemopure® samples were analyzed hourly. The perfusate was oxygenated using an external mixed air supply (35% $O_2$, 2 L/min). After reperfusion with stressed blood, kidneys were bivalved sagittally. One half was stored at −80° C. for mechanistic analyses and the other half was stored in formalin for histopathological analyses.

A non-limiting example of a perfusate composition is detailed in Table 1.

TABLE 1

Perfusate composition for preservation and reperfusion

| Preservation Perfusate Composition: | Reperfusion Perfusate Composition: |
|---|---|
| 250 mL Hemopure ® | 250 mL Hemopure ® |
| 750 mL Plasmalyte | 750 mL Plasmalyte |
| Initial additions to Perfusate: | Initial additions to Perfusate: |
| 5000 IU Heparin | 5000 IU Heparin |
| 20 mL Sodium Bicarbonate | 20 mL Sodium Bicarbonate |
| 1 g Ancef | 1 g Ancef |
| AP39 to the AP39 group only | 1.5 g Dextrose |
| STS to the STS group only | 4 g Mannitol |
| | 10 mg Creatinine |
| | Continuous drips: |
| | 1.5 g/hr of Dextrose (5% Dextrose solution, 0.5 mL/min) |
| | 7 IU/hr of Insulin (50 IU Insulin diluted in 250 mL Saline, 0.6 mL/min) |

Sample Collection and Analysis of Graft Renal Function and Injury

Hemopure® and urine samples were collected hourly during the 4 h preservation perfusion and during the 4 h reperfusion to evaluate graft function over time. Electrolyte levels, lactate levels and gas levels in the perfusate were measured hourly using the iSTAT point-of-care testing system. Hourly urine output was recorded, and total urine samples were also collected from both perfusion periods. Pictures of the kidney, urine bags and flow and pressure readings were taken hourly. Tissue oxygenation was also measured hourly. During both perfusion periods, we closely monitored pump parameters (flow and pressure) to ensure optimal graft function.

Hemopure®

Hemopure® (aka HBOC-201) was generously provided by HbO2 therapeutics (Pennsylvania, USA). A new bag of Hemopure® (250 mL) was used for each 4 h period of preservation perfusion and reperfusion. A mixture of Hemopure (250 mL) and Plasmalyte (750 mL) was used for perfusion in order to achieve the volume (1L) required to run the ex vivo perfusion circuit. AP39 and STS treatments were applied during preservation perfusion at 21° C. as described below. During reperfusion at 37° C., the following were added to the perfusate solution: heparin (5 mL), bicarb (20 mL), ancef (1 g), mannitol (4 g), creatinine (10 mg) and an initial bolus of dextrose (1.5 mg). During the 4 h of reperfusion, a continuous dextrose (0.5 mL/min, 5% dextrose in water) and insulin drip (0.6 mL/min, 50 IU insulin in 250 mL of saline) was maintained to facilitate kidney metabolism.

AP39

AP39, generously provided by Dr. Whiteman (Exeter, UK), was dissolved in dimethyl sulfoxide to achieve a 1 mM stock concentration. 200 µL of the stock was added to 1L bags of preservation solution used for flushing, and Hemopure®:plasmalyte mixture used for perfusion, to achieve a treatment concentration of 200 nM AP39. 1 mL of the stock was added to 1L bags of preservation solution used for flushing, and Hemopure®:plasmalyte mixture used for perfusion, to achieve a treatment concentration of 1 µM AP39.

STS

Seacalphyx, sodium thiosulfate (STS) pentahydrate injection, was dispensed by the London Health Sciences centre pharmacy. 150 µL of the drug was added to 1L bags of preservation solution used for flushing, and Hemopure®: plasmalyte mixture used for perfusion, to achieve a treatment concentration of 150 µM STS.

Histopathology Imaging and Quantification

The formalin-fixed kidney sections were stained with Terminal deoxynucleotidyl transferase dUTP nick end labeling (TUNEL) along with Hematoxylin and Eosin (H&E) to determine the level of apoptosis and acute tubular necrosis (ATN) respectively. TUNEL and H&E imaging was done using the Nikon Instruments Eclipse 90i digital microscope at 10× magnification (Nikon Instruments, New York). To quantify apoptotic injury and ATN, TUNEL and H&E slides were scored by a blinded renal pathologist as per the following scheme: 1=<11%, 2=11-24%, 3=25-45%, 4=46-75%, 5=>75%.

Data Analysis

All statistical analyses were conducted using GraphPad Prism Version 8. To compare the graft function and graft injury outcomes of two treatment groups, t-tests were performed. To compare the graft function and graft injury outcomes of three treatment groups, one-way ANOVA and Tukey's post-hoc test were performed. Statistical significance was accepted at $p<0.05$.

Results

Figure 1:
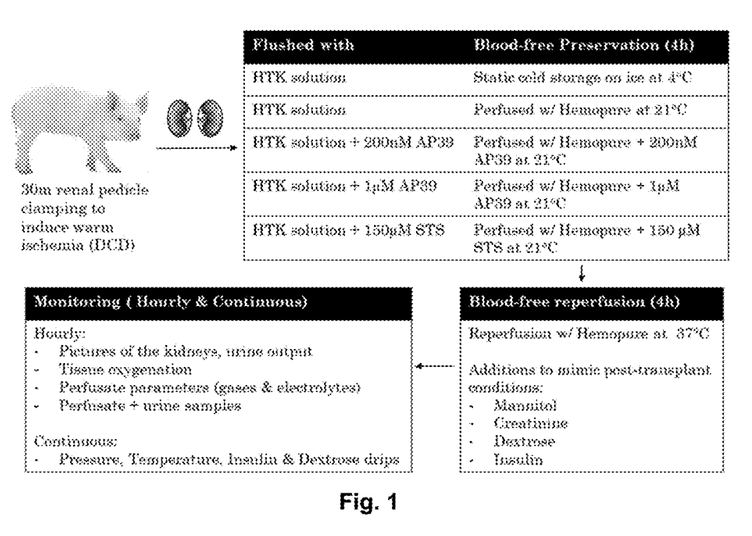
FIG. 1 Summary of the methods used to establish and optimize blood-free preservation and reperfusion.
Figure 2:
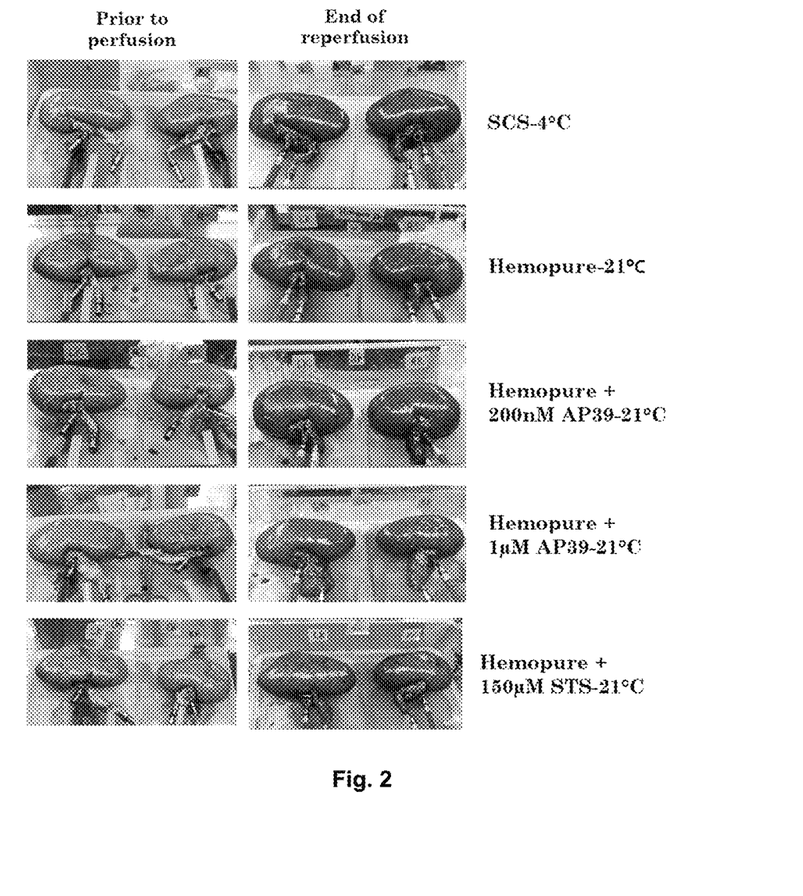
FIG. 2. Experiment images taken prior to reperfusion and at the end of reperfusion. Images were taken prior to perfusion (left-column images) to document consistency in ischemic injury and flushing of the kidneys. Images were taken at the end of reperfusion (4 h) to document colour and swelling at the end of the experiments (right-column images).

With reference to FIG. 2, the photographs in the left column were taken prior to perfusion to document consistency in ischemic injury and flushing of the kidneys. The photographs in the right column of FIG. 2 were taken at the end of reperfusion (4 h) to document colour and swelling at the end of the experiments.

Figure 3A:
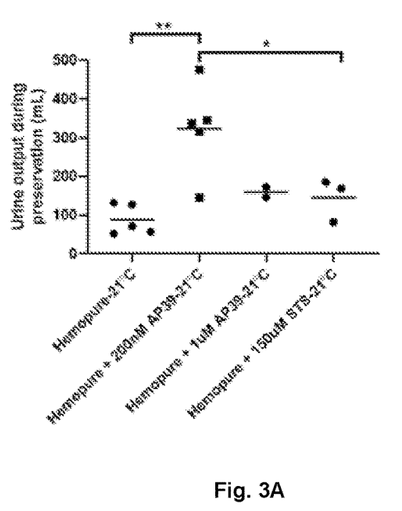
FIGS. 3A-3B Total urine output during preservation, and total urine output during reperfusion. (3A) Total urine output (mL) during 4 h of preservation perfusion with Hemopure®, Hemopure®+200 nM AP39, Hemopure®+1 µM AP39 or Hemopure®+150 µM STS at 21° C. (3B) Total urine output (mL) during 4 h of reperfusion with Hemopure® and nutrients at 37° C. after 4 h of preservation via SCS on ice at 4° C. or perfusion with Hemopure®, Hemopure®+200 nM AP39, Hemopure®+1 µM AP39 or Hemopure®+150 µM STS at 21° C. Points in (3A) and (3B) reflect urine outputs of individual kidneys and lines represent the mean. Values were compared using one-way ANOVA. *, $p<0.05$. , $p<0.01$, *, $p<0.001$.
Figure 3B:
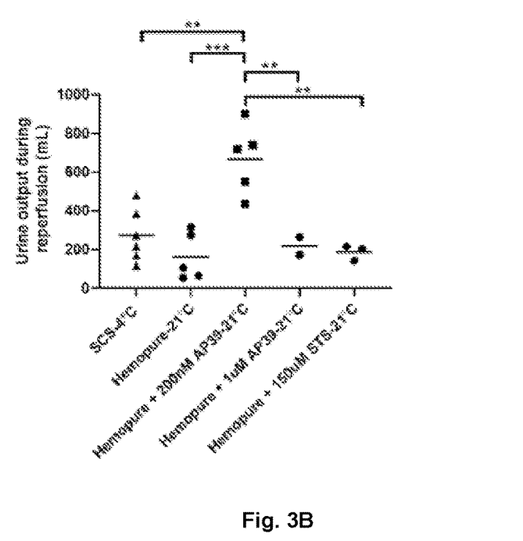

Subnormothermic perfusion with Hemopure® and 200 nm AP39, resulted in significantly higher urine output ($p<0.01$) during preservation than perfusion with Hemopure® (FIG. 3A). Subnormothermic perfusion with Hemopure® and 200 nm AP39, Hemopure® and 1 μM AP39 and Hempure and 150 μM STS resulted in significantly higher urine output (p0.05) than perfusion with Hempure® (FIG. 3A). During reperfusion, Hemopure®+200 nm AP39 kidneys exhibited significantly higher urine output ($p<0.01$) than Hemopure® kidneys (FIG. 3B).

Figure 4B:
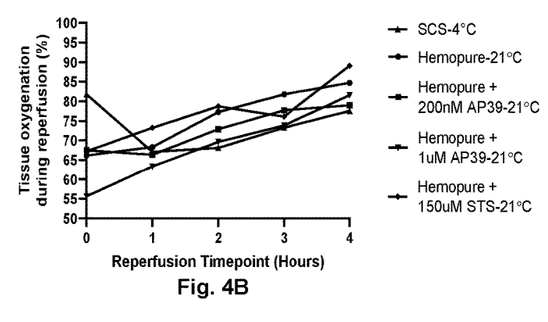
Figure 5A:
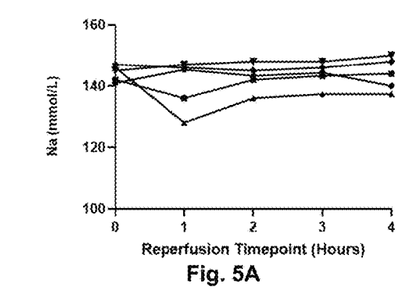
FIGS. 5A-5F. Perfusate parameters over time during 4 h of reperfusion with Hemopure® and nutrients. Hemopure® perfusate samples were collected hourly during reperfusion and analyzed with the iSTAT machine for chemistry and gas composition. (A) Mean perfusate $Na^+$ (mmol/L) during reperfusion. (B) Mean perfusate (mmol/L) during reperfusion. Each point represents mean levels of the parameter of all experiments in that group at that timepoint. (C) Mean perfusate pH during reperfusion. (D) Mean perfusate lactate (mmol/L) during reperfusion. (E) Mean perfusate $pO_2$ (mmHg) during reperfusion. (F) Mean perfusate $pCO_2$ (mmHg) during reperfusion.
Figure 5B:
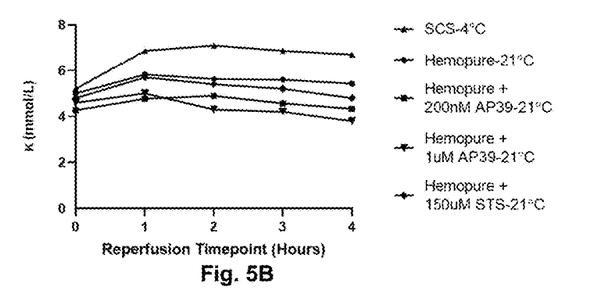
Figure 5C:
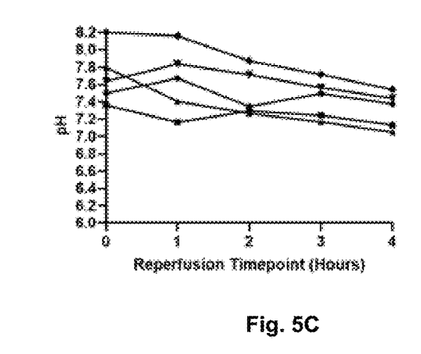
Figure 5D:
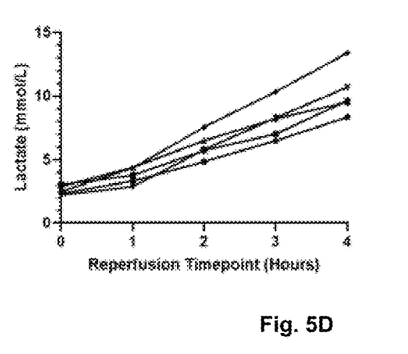
Figure 5E:
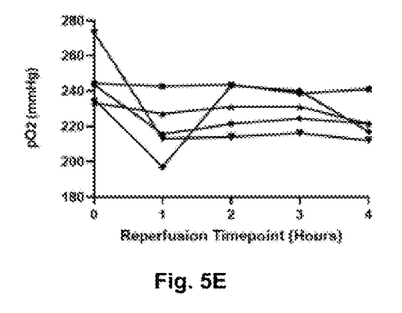
Figure 5F:
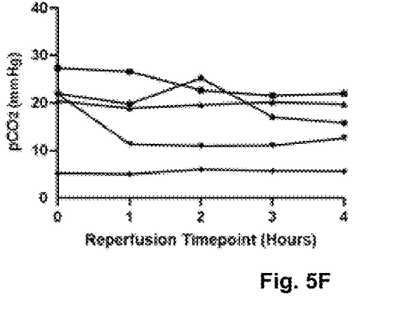
Figure 6A:
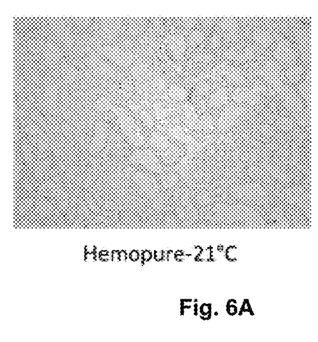
FIGS. 6A-6F. Apoptotic injury following preservation and reperfusion. Kidney sections, collected after reperfusion, were fixed in formalin were stained with TUNEL to determine apoptotic injury. A) to (E) are representative TUNEL images taken at 10× magnification for each of the 5 preservation treatment groups. (F) TUNEL scores as assigned by a blinded renal pathologist: 1=<11%, 2=11-24%, 3=25-45%, 4=46-75%, 5=>75%. Points in (F) represent the TUNEL score for individual kidneys and the lines represent the mean. Values were compared using one-way ANOVA. *, $p<0.05$. **, $p<0.01$.
Figure 6B:
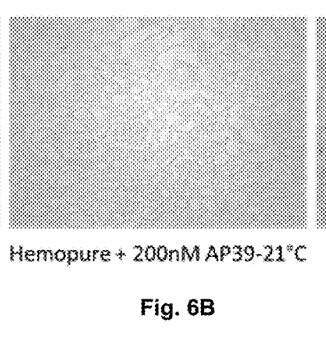
Figure 6C:
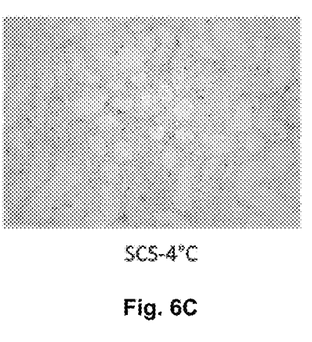
Figure 6D:
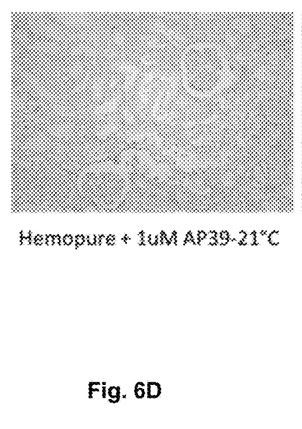
Figure 6E:
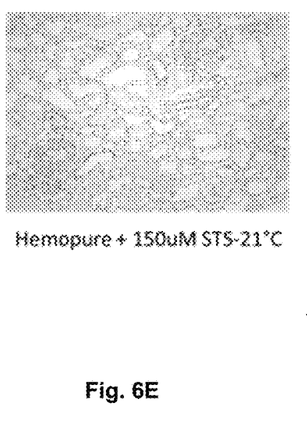
Figure 6F:
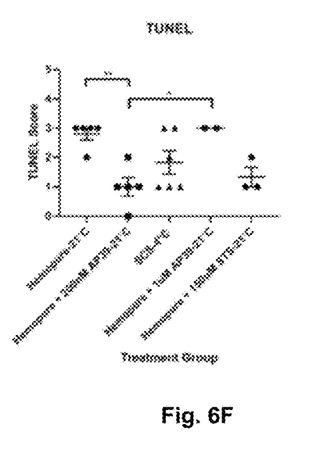
Figure 7A:
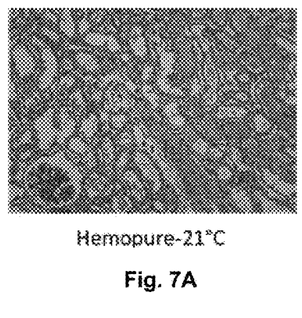
FIGS. 7A-7F. Acute tubular necrosis following preservation and reperfusion. Kidney sections, collected after reperfusion, were fixed in formalin were stained with H&E to determine apoptotic injury. A) to (E) are representative H&E images taken at 10× magnification for each of the 5 preservation treatment groups. (F) ATN scores as assigned by a blinded renal pathologist: 1=<11%, 2=11-24%, 3=25-45%, 4=46-75%, 5=>75%. Points in (F) represent the H&E score for individual kidneys and the lines represent the mean. Values were compared using one-way ANOVA. *, $p<0.05$. **, $p<0.01$.
Figure 7B:
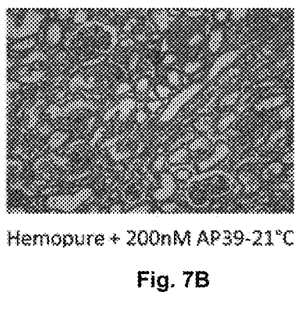
Figure 7C:
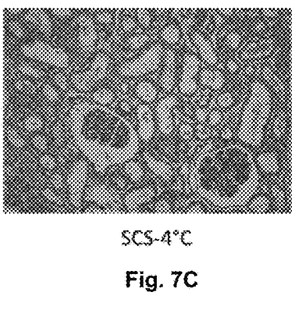
Figure 7D:
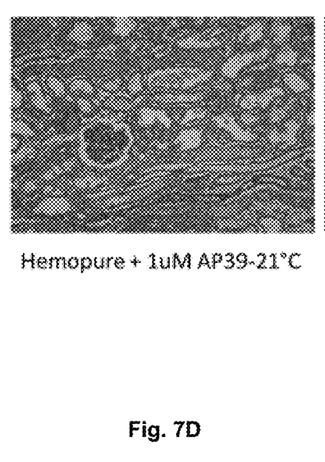
Figure 7E:
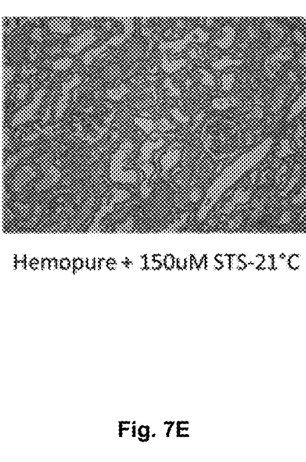
Figure 7F:
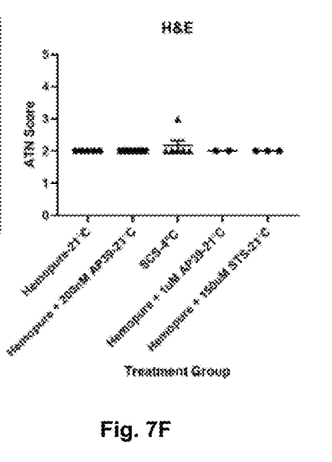
Figure 8:
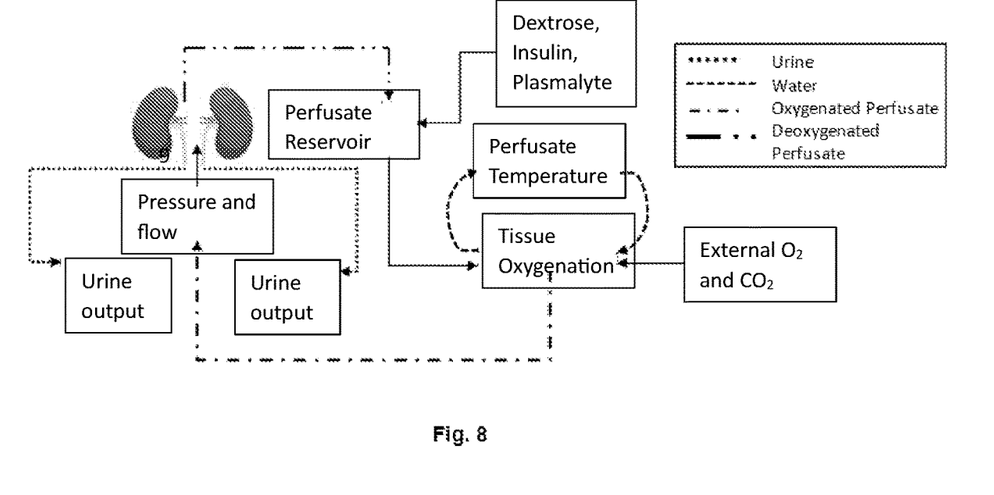
FIG. 8. Illustration of an ex vivo perfusion setup.

Preservation with Hempure and 150 μM STS and Hemopure®+200 nm AP39 led to higher tissue oxygenation than SCS (FIG. 4A). Tissue oxygenation levels were comparable for all groups (FIG. 4B).

FIGS. 5A to 5F show that that the perfusate composition is similar between all groups and that Na (FIG. 5A), K (FIG. 5B), pO2 (FIG. 5E), pCO2 (FIG. 5F) and pH (FIG. 5C) are maintained within biological ranges. The lactate values (FIG. 5D) show that injury increases over time in all groups. FIGS. 6A to 6F show that Hemopure®+200 nm AP39 reduced apoptotic tissue injury compared to Hemopure® and Hemopure®+1 μm AP39. FIGS. 7A to 7F show that acute tubular necrosis scores were comparable for all groups.

Our research has also found that ex vivo perfusion of DCD porcine kidneys with AP39-supplemented blood at 21° C. improves graft function compared to cold storage in UW and perfusion with only blood at 21° C. and 37° C. The use of blood, however, is complicated and a new hemoglobin-based blood substitute, Hemopure®, works better than blood in our ex vivo perfusion set up at 21° C. The overall aim is to optimize subnormothermic preservation using the most advanced models of DCD renal transplantation.

It is well known that one of the most important parameters that reflect proper organ perfusion is the hourly urine output. For the first time it is demonstrated that subnormothermic perfusion at 21° C. with an oxygen carrier+$H_2S$ improves renal outcomes compared to SCS (standard of care), using a blood-free model of preservation and reperfusion. This disclosure is useful for pre-transplant evaluation of discarded grafts to maximize the utilization of marginal kidneys.

A skilled person in the art does not expect the oxygenation to change as $H_2S$ is not an $O_2$ donor. However, one skilled in the art would also not expect the oxygenation of tissue to be maintained with $H_2S$ as $H_2S$ is known to be an oxygen antagonist. $H_2S$ decreases tissue injury by creating more ATP during ischemic stress and likely causes vasodilation so flow is better, so urine output increase could be due to both of those factors since the kidney is healthier and less injured. We have injury scores for kidneys stored in $H_2S$ versus UW solution whereby the tissue injury is remarkably less in the $H_2S$ kidneys, so we know that even during storage there is repair. We also recently obtained cell free DNA data which also holds true for the current disclosure.

The Hemopure® component of the disclosure provides oxygen-carrying capacity as it is composed of purified bovine hemoglobin, which will limit the use of blood for normothermic and subnormothermic organ preservation. The AP39 component of the disclosure serves as the $H_2S$ donor, which will help facilitate the delivery of $H_2S$ to maximize graft viability. AP39 has been shown to be effective at very low concentrations and it has diverse protective effects (anti-oxidant, anti-apoptotic, antioxidant, etc.). We have previously shown that adding AP39 to cold preservation solutions improves renal graft outcomes. Our most recent study looking at subnormothermic perfusion with the disclosure (Hemopure®+AP39) has shown that it is superior to perfusion with Hemopure® alone and static cold storage.

In addition, these findings are not clearly obvious as the efficiency of $H_2S$ donor molecules appears to be more important at low oxygen tensions, however, in the case of the Hemopure® combination findings, the oxygen tension is high, which should in fact be deleterious to $H_2S$ therapy. Therefore, a combination of the two substances creates a novel and clearly important new solution that is widely applicable to a variety of clinical scenarios, including renal transplantation.

Example 2

Surgery & Induction of Warm Ischemia to Mimic Donation after Cardiac Death

Pigs were tranquilized prior to transport to the Canadian Surgical Technologies & Advanced Robotics facility (CSTAR, University Hospital, London, Canada). Upon arrival at CSTAR, the animals were prepared for surgery as per SOP. A midline incision was used to expose the kidneys. The right and left kidneys with their ureters were dissected free from the retro peritoneum while leaving the blood supply to the ureter intact and then the ureter was divided. The renal vascular pedicles were left as long as possible by freeing the renal artery and vein up to the aorta and vena cava. The pedicles were clamped for 30 minutes to induce warm ischemia in the donor organs following intravenous infusion of 3000 units of heparin. The injury inflicted is likely greater than that of conventional DCD kidneys after withdrawal of life support as the blood supply is cutoff completely by clamping, which is more harmful than the gradual ischemic injury that occurs during cardiac death. Subsequently, nephrectomies of the left and right kidney were performed and the donor animal was euthanized. Autologous blood used for the preservation perfusion and the reperfusion period was collected via cannulation of the inferior vena cava before clamping of the renal pedicles (non-stressed blood) and after clamping (stressed blood). All the surgeries were performed by transplant fellows at University Hospital, London, Ontario, Canada.

Ex Vivo Organ Preservation Treatments & Reperfusion to Mimic Transplantation

The kidneys were randomly assigned to one of four preservation treatments. The first group of kidneys were flushed with and stored in UW solution on ice (SCS-4° C.) for 4 h, which reflects the current clinical standard of care for organ preservation. The second group of kidneys were flushed with UW solution supplemented with 200 nM AP39 and perfused with non-stressed blood supplemented with 200 nM AP39 at 21° C. for 4 h (SMP-AP39-21° C.). As controls, the third group of kidneys were perfused with non-stressed blood at 21° C. (SMP-21° C.) and the fourth group of kidneys were perfused with non-stressed blood at 37° C. (NMP-37° C.) after being flushed with UW solution. After the 4 h preservation period, all kidneys were perfused with stressed autologous blood for 4 h at 37° C. to simulate reperfusion (restoration of blood flow) after renal transplantation. The kidneys were perfused using an ex vivo perfusion apparatus under the supervision of a cardiovascular perfusionist. The perfusion pressure was maintained within 40-50 mmHg. The non-stressed and stressed blood used in the perfusion circuits was oxygenated using an external mixed air supply (35% $O_2$, 2 L/min). Blood, urine and tissue samples were collected and analyzed as described in the next subsection.

Sample Collection and Analysis of Graft Renal Function and Injury

Blood and urine samples were collected hourly during the 4 h preservation perfusion with non-stressed blood and during the 4 h reperfusion with stressed blood to evaluate graft function over time. Hourly urine output was recorded, and total urine samples were also collected from both perfusion periods. Pictures of the kidney, urine bags and blood flow and pressure readings were taken hourly. The blood and urine samples were sent to the LHSC core laboratory for routine analysis. During the perfusion periods, we closely monitored pump parameters (flow and pressure) to ensure optimal graft function. After reperfusion with stressed blood, they kidneys were stored in formalin for a minimum of 72 hours. Histopathological analysis was performed on the formalin-fixed kidney sections by staining with Terminal deoxynucleotidyl transferase dUTP nick end labeling (TUNEL) to determine the level of apoptosis. All images were taken at 10× magnification using a Nikon Eclipse 90i light microscope (Nikon, Canada). The total TUNEL+ area (%) was quantified for 10 random fields of view for 2 kidney samples per treatment group using ImageJ software v 1.50 (National Institutes of Health, USA). The total tubular area and TUNEL+ tubular area, used to calculate the TUNEL+ area (%), were determined by adjusting the brightness and saturation thresholds.

Data Analysis

All statistical analyses were conducted using GraphPad Prism Version 7. To compare the graft function and graft injury outcomes of two treatment groups, t-tests were performed. To compare the graft function and graft injury outcomes of three treatment groups, one-way ANOVA and Tukey's post-hoc tests were performed. Statistical significance was accepted at $p<0.05$.

Results

Figure 9A:
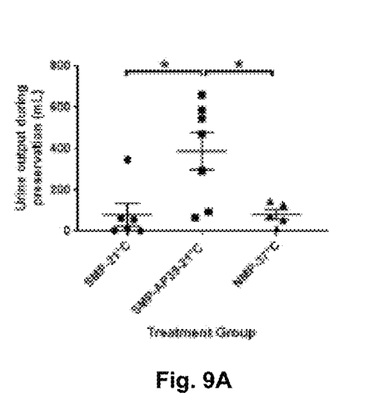
FIGS. 9A-9D Total urine output during preservation and reperfusion along with tissue injury following reperfusion. (5A) Total urine output during 4 h of preservation perfusion with non-stressed blood at 21° C., non-stressed blood at 37° C., or non-stressed blood at 21° C. with 200 nM AP39. (5B) Total urine output during 4 h of reperfusion with stressed blood at 37° C. after 4 h of preservation via SCS on ice at 4° C. or perfusion with non-stressed blood at 21° C., non-stressed blood at 37° C., or non-stressed blood at 21° C. with 200 nM AP39. Points in (5A) and (5B) reflect urine outputs of individual kidneys and lines represent the mean±SEM for the group. (5C) Mean TUNEL+ area reflective of apoptotic injury. Each point in (C) reflects the mean TUNEL+ area of one kidney through quantification values from 10 images and lines represent mean±SEM for the group. (5D) Mean acute tubular necrosis (ATN) score. Each point in D is a score assigned by a blinded renal pathologist to an H&E slide of individual kidneys and the lines represent mean±SEM for the group.

With reference to FIG. 9A, subnormothermic perfusion at 21° C. with AP39-supplemented blood (SMP-AP39-21C) led to significantly higher urine output during 4 h of preservation than subnormothermic perfusion (SMP-21C) and normothermic perfusion at 37° C. (NMP-37C) with just blood.

Figure 9B:
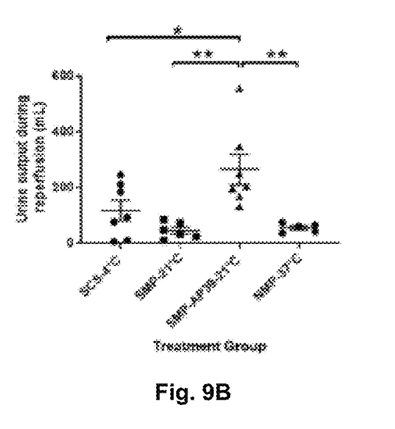

As seen in FIG. 9B During 4 h of reperfusion with stressed blood, kidneys preserved with SMP-AP39-21C exhibited significantly higher urine output than kidneys preserved via SCS-4C (static cold storage), SMP-21C, NMP-37C.

Figure 9C:
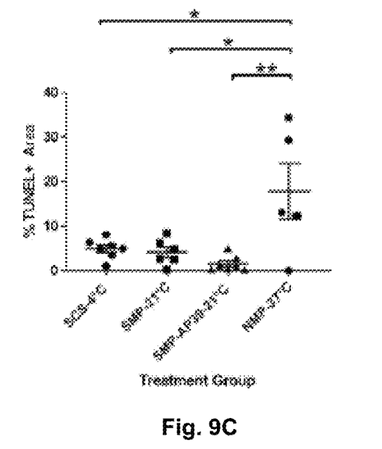
Figure 9D:
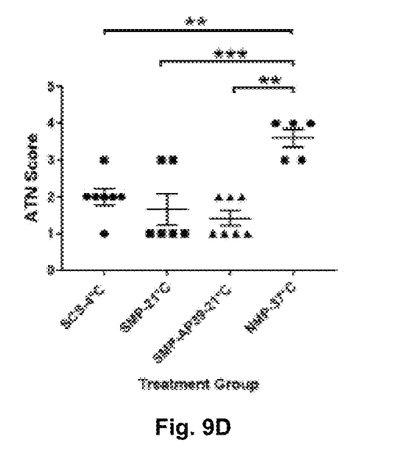

FIGS. 9C and 9D show that NMP-37C led to significantly higher apoptosis injury and necrosis than all other groups.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

REFERENCES

1. Juriasingani S, Akbari M, Luke P, Sener A. Novel therapeutic strategies for renal graft preservation and their potential impact on the future of clinical transplantation [Internet]. Vol. 24, Current Opinion in Organ Transplantation. Lippincott Williams and Wilkins; 2019 [cited 2020 Apr. 7]. p. 385-90.
2. Juriasingani S, Akbari M, Chan J Y, Whiteman M, Sener A. H2S supplementation: A novel method for successful organ preservation at subnormothermic temperatures. Nitric Oxide [Internet]. 2018 Dec. 1 [cited 2019 Feb. 10]; 81:57-66.
3. Szczesny B, Modis K, Yanagi K, Coletta C, Le Trionnaire S, Perry A, Wood M, Whiteman M, Szabo C. AP39, a novel mitochondria-targeted hydrogen sulfide donor, stimulates cellular bioenergetics, exerts cytoprotective effects and protects against the loss of mitochondrial DNA integrity in oxidatively stressed endothelial cells in vitro. Nitric Oxide. 2014 Sep. 15; 41: 120-30.
4. Bhattacharjee R N, Ruthirakanthan A, Sun Q, Richard-Mohamed M, Luke S, Jiang L, Aquil S, Sharma H, Tun-Abraham M E, Alharbi B, Haig A, Sener A, Luke P P W. Subnormothermic Oxygenated Perfusion Optimally Preserves Donor Kidneys Ex Vivo. Kidney Int Reports. 2019 Sep. 1; 4(9):1323-33.
5. Bhattacharjee R N, Patel S V B, Sun Q, Jiang L, Richard-Mohamed M, Ruthirakanthan A, Aquil S, Al-Ogaili R, Juriasingani S, Sener A, Luke P P W. Renal Protection Against Ischemia Reperfusion Injury: Hemoglobin-based Oxygen Carrier-201 Versus Blood as an Oxygen Carrier in Ex Vivo Subnormothermic Machine Perfusion. Transplantation. 2020 March; 104(3): 482-489.
6. Hoyer D P, Gallinat A, Swoboda S, Wohlschlager J, Rauen U, Paul A, Minor T. Subnormothermic machine perfusion for preservation of porcine kidneys in a donation after circulatory death model. Transpl Int [Internet]. 2014 October [cited 2018 Apr. 12]; 27(10):1097-106.

What is claimed is:

1. A tissue oxygenation composition comprising (a) a solution containing an artificial oxygen carrier and (b) hydrogen sulfide ($H_2S$).

2. The tissue oxygenation composition of claim 1, wherein the artificial oxygen carrier is a hemoglobin-based oxygen carrier (HBOC), perfluorocarbon-based oxygen carrier (PFOC) or an artificial oxygen carrier derived from stem cells (SCs).

3. The tissue oxygenation composition of claim 1, wherein the $H_2S$ is provided as a $H_2S$ donor.

4. The tissue oxygenation composition of claim 3, wherein the $H_2S$ donor is AP39 or sodium thiosulfate (STS).

5. A method of preserving or reperfusing tissue, the method comprising storing or reperfusing the tissue with a composition comprising (a) an oxygenated-solution or a solution containing an oxygen carrier and (b) hydrogen sulfide ($H_2S$).

6. The method of claim 5, wherein the composition comprises the solution containing the oxygen carrier, the oxygen carrier is a hemoglobin-based oxygen carrier or blood, and wherein the $H_2S$ is provided as a $H_2S$ donor.

7. The method of claim 6 wherein the $H_2S$ donor is AP39 or sodium thiosulfate (STS).

8. The method of claim 5, wherein the storing or reperfusing is carried out at subnormothermic temperatures or normothermic temperatures.

9. A method of maintaining tissue oxygenation during tissue preservation or reperfusion, the method comprising storing or reperfusing the tissue with a composition comprising (a) an oxygenated-solution or a solution containing an oxygen carrier and (b) hydrogen sulfide ($H_2S$).

10. The method of claim 9, wherein the composition comprises the solution containing the oxygen carrier, the oxygen carrier is a hemoglobin-based oxygen carrier or blood, and wherein the $H_2S$ is provided as a $H_2S$ donor.

11. The method of claim 10 wherein the $H_2S$ donor is AP39 or sodium thiosulfate (STS).

12. The method of claim 9, wherein the storing or reperfusing is carried out at subnormothermic temperatures or normothermic temperatures.

13. A method of decreasing the incidence and duration of delayed graft function during organ transplantation, the method comprising contacting an organ to be transplanted with a composition comprising (a) an oxygenated solution or a solution containing an oxygen carrier and (b) hydrogen sulfide ($H_2S$).

14. The method of claim 13, wherein the composition comprises the solution containing the oxygen carrier, the oxygen carrier is a hemoglobin-based oxygen carrier or blood, and wherein the $H_2S$ is provided as a $H_2S$ donor.

15. The method of claim 13, wherein the contacting is carried out at subnormothermic temperatures or normothermic temperatures.

16. A method of treating an ischemic event in a subject, the method comprising administering to the subject or contacting a tissue of the subject with the composition of claim 1.

17. The method of claim 16, wherein the ischemic event is an ischemic injury.

18. The method of claim 16, wherein the ischemic event includes myocardial infarction, trauma, hypovolemic shock, compartment syndrome, stroke, or sepsis.

19. The method of claim 16, wherein the $H_2S$ is provided as a $H_2S$ donor.

20. The method of claim 19, wherein the $H_2S$ donor is AP39 or sodium thiosulfate (STS).

* * * * *